United States Patent
Sawyer et al.

(10) Patent No.: US 11,197,946 B2
(45) Date of Patent: Dec. 14, 2021

(54) FABRICATION OF AUTOLOGOUS BONE

(71) Applicant: University of Florida Research Foundation, Inc., Gainesville, FL (US)

(72) Inventors: Wallace Gregory Sawyer, Gainesville, FL (US); Thomas Ettor Angelini, Gainesville, FL (US); Steven C. Ghivizzani, Gainesville, FL (US); C. Parker Gibbs, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 16/347,725

(22) PCT Filed: Nov. 7, 2017

(86) PCT No.: PCT/US2017/060357
§ 371 (c)(1),
(2) Date: May 6, 2019

(87) PCT Pub. No.: WO2018/085821
PCT Pub. Date: May 11, 2018

(65) Prior Publication Data
US 2019/0255222 A1      Aug. 22, 2019

Related U.S. Application Data

(60) Provisional application No. 62/418,570, filed on Nov. 7, 2016.

(51) Int. Cl.
*A61L 27/38* (2006.01)
*A61F 2/28* (2006.01)

(52) U.S. Cl.
CPC ............ *A61L 27/3847* (2013.01); *A61F 2/28* (2013.01); *A61L 27/3834* (2013.01); *A61L 27/3821* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 2006/0149362 A1* | 7/2006 | Pedrozo | A61F 2/04 623/1.35 |
| 2015/0343117 A1* | 12/2015 | Ling | A61L 27/56 424/423 |
| 2018/0258382 A1* | 9/2018 | Keselowsky | C12M 33/00 |

OTHER PUBLICATIONS

Bhattacharjee et al., Liquid-like Solids Support Cells in 3D, ACS Biomater. Sci. Eng. 2, p. 1787-1795, 2016.
International Search Report issued for PCT/US2017/060357, dated Feb. 1, 2018.

* cited by examiner

*Primary Examiner* — H. Sarah Park
(74) *Attorney, Agent, or Firm* — Thomas|Horstemeyer LLP

(57) ABSTRACT

Described herein are methods and apparatus for constructing tissue replacements, such as bone replacements that may be used to repair damaged or missing segments of bone, such as may occur in wound repair or as a repair of a congenital anomaly. These methods involve a three-dimensional (3D) cell growth medium made from a yield stress material that allows cells and structures to be easily deposited and positioned.

12 Claims, 7 Drawing Sheets

FABRICATION OF AUTOLOGOUS BONE

CROSS-REFERENCE TO RELATED APPLICATIONS

This application claims benefit of U.S. Provisional Application No. 62/418,570, filed Nov. 7, 2016, which is hereby incorporated herein by reference in its entirety.

TECHNICAL FIELD

Disclosed embodiments are related to bioengineering autologous bone grafts.

BACKGROUND

Skeletal bone has a remarkable capacity for self-repair, but in cases of severe trauma (e.g. blast injury) or cancer surgery, where large segments of bone have either been destroyed or removed, full functional repair requires the implantation of exogenous bone graft with appropriate dimensions and load-bearing capabilities. Vascularized autogenous bone is the gold standard, as it readily assimilates into neighboring tissues, and fully remodels into healthy tissue. Since the supply of healthy bone available for harvest is limited, decellularized bone from cadaveric donors is frequently used to repair large scale defects. It provides the native structure, composition and mechanical support, but due to the lack of vascularity it fails to remodel into living tissue and becomes brittle and vulnerable to fracture.

Use of three-dimensional scaffold as a template for cell regeneration is foundational to tissue engineering. Identification of the relationship of cell response on a two-dimensional (2D) surface to that of a three-dimensional (3D) object is increasingly important as biotechnology moves from conventional 2D to 3D cell cultures, which better mimic their in vivo counterparts.

Current state of the art generation of micron-to-millimeter scale surface topography relies on micropatterning, lithography techniques, or rapid prototyping based on the integration of 3D computer-aided design (CAD) and 3D printing or an additive layer method, which require specialized equipment or facilities, and often involve tedious procedures. Substrates with complex geometry, such as cylindrical, toroidal, and spherical scaffolds are challenging and time-consuming to fabricate with the aforementioned methods. Existing scaffold processing techniques have evolved from the more traditional subtractive approaches, which involve constant removal of materials, to conventional additive approaches, which utilize solid free form fabrication by selectively adding materials layer by layer. Current commercially available 3D printing systems involve printing a solid support at the same time as the printed structure, layer by layer. After printing, the support material is washed away and discarded.

One free forming technique is electrospinning, a method that produces nonwoven fibrous structures with fiber diameters in the range of tens of nanometer to a micrometer. The polymer solution used is fed through a syringe and extruded from the spinneret (needle tip) connected to a high-voltage, where the nanofibers are generated. The 3D printing technique also utilizes a dispensing nozzle (inkjet print head) in its free forming process to deposit polymer powder and binding liquid in each layer.

SUMMARY

Described herein are methods and apparatus for constructing tissue replacements, such as bone replacements that may be used to repair damaged or missing segments of bone, such as may occur in wound repair or as a repair of a congenital anomaly. These methods involve a three-dimensional (3D) cell growth medium made from a yield stress material that allows cells and structures to be easily deposited and positioned. In some cases, this involves a solid to liquid phase change at a desired location in a region of yield stress material such that the yield stress material will flow and be displaced when cells or structures are placed at the desired location. Once completed, it then transforms back into a solid-like phase to support the cells and/or structures. In particular, the disclosed 3D growth medium allows for placement of tissue scaffolds and vascular structures to produce vascularized tissue replacements.

Therefore, disclosed herein is a method for engineering vascularized tissue that involves first providing a 3D cell growth medium comprising a plurality of hydrogel particles and a liquid cell culture medium, wherein the hydrogel particles are swelled with the liquid cell culture medium to form a granular gel.

The method can then involve depositing into the granular gel a biocompatible support scaffold. This scaffold can be natural or synthetic. For example, the scaffold can be derived from an autologous, allogenic or xenogenic graft. In other embodiments, the scaffold is engineered using biocompatible materials. For example, in some cases, the scaffold is producing by 3D printing, which can be done prior to deposit into the granular gel, or can be printed directly in the granular gel. For example, where the tissue is bone, the support scaffold can be a mineralized scaffold. In some cases, the support scaffold comprises decellularized bone, e.g. from a cadaveric donor. In other cases, the support scaffold comprises a porous scaffold formed from an osteogenic, osteoconductive, and/or osteoinductive material. For example, the scaffold can comprise hydroxyapatite.

The method can also involve depositing into the granular gel a vascular structure capable of supporting blood flow. This can be done before, after, or simultaneously with the deposit of the scaffold. The vascular structure has a proximal and distal end in fluid communication. Therefore, in preferred embodiments, the distal end of the vascular structure is positioned in the granular gel in a location suitable to provide oxygen to the scaffold if blood is pumped into the proximal end of the vascular structure. In some embodiments, the vascular structure comprises an arterial or venous segment from a subject. In other embodiments, the vascular structure is a tissue engineered vessel. For example, the vessel can be produced using autologous or allogenic endothelial cells, progenitor cells, or stem cells.

The method can also optionally involve depositing into the granular gel a cellular component. This can be done before, after, or simultaneously with the deposit of the scaffold and/or the vascular structure. The choice of cellular component depends on the type of tissue being engineered. In some cases, the cellular component comprises one or more stem cells or progenitor cells capable of forming the desired tissue in the support scaffold. The cellular component can be positioned, for example, in the support scaffold, or between the support scaffold and the vascular structure. For example, where the tissue is bone, the cellular component can comprise bone marrow cells, or marrow-like cells. Therefore, in some embodiments, the cellular component comprises mesenchymal stem cells (MSCs), hematopoietic stem cells (HSCs), osteoblasts, osteocytes, angioblasts, or any combination thereof. The cellular component can further comprises growth factors selected from vascular endothelial growth factor (VEGF), basic fibroblast growth factor (bFGF), epidermal growth factor (EGF), or any combination thereof.

The method can then involve attaching a flow device to the proximal end of the vascular structure and flowing through the vascular structure a blood-like media sufficient to support tissue growth. In some embodiments, the blood-like media comprises blood or a blood substitute comprising oxygenated erythrocytes.

In some embodiments, the cellular component is pumped through the vascular structure instead of depositing it directly into the granular gel. Likewise, in some embodiments, growth factors are pumped through the vascular structure. A growth factor gradient can also be created in the granular gel.

In some embodiments, the three-dimensional cell growth medium has a yield stress such that the cell growth medium undergoes a phase change from a first solid phase to a second liquid phase upon application of a shear stress greater than the yield stress. For example, the yield stress can be on the order of 10 Pa+/−25%. In some cases, the concentration of hydrogel particles is between 0.05% to about 1.0% by weight. In some embodiments, the hydrogel particles have a size in the range of about 0.1 µm to about 100 µm when swollen with the liquid cell culture medium. In some cases, the hydrogel particles have a size in the range of about 1 µm to about 10 µm when swollen with the liquid cell culture medium.

In some embodiments, there are molecules diffused into the granular gel particles and throughout the granular gel. For example, the molecules can be small molecules or proteins (e.g. growth factors). In some cases, the molecules are small molecules, and wherein the small molecules comprise nutrients or dissolved gasses.

The details of one or more embodiments of the invention are set forth in the accompanying drawings and the description below. Other features, objects, and advantages of the invention will be apparent from the description and drawings, and from the claims.

DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

Figure 1:
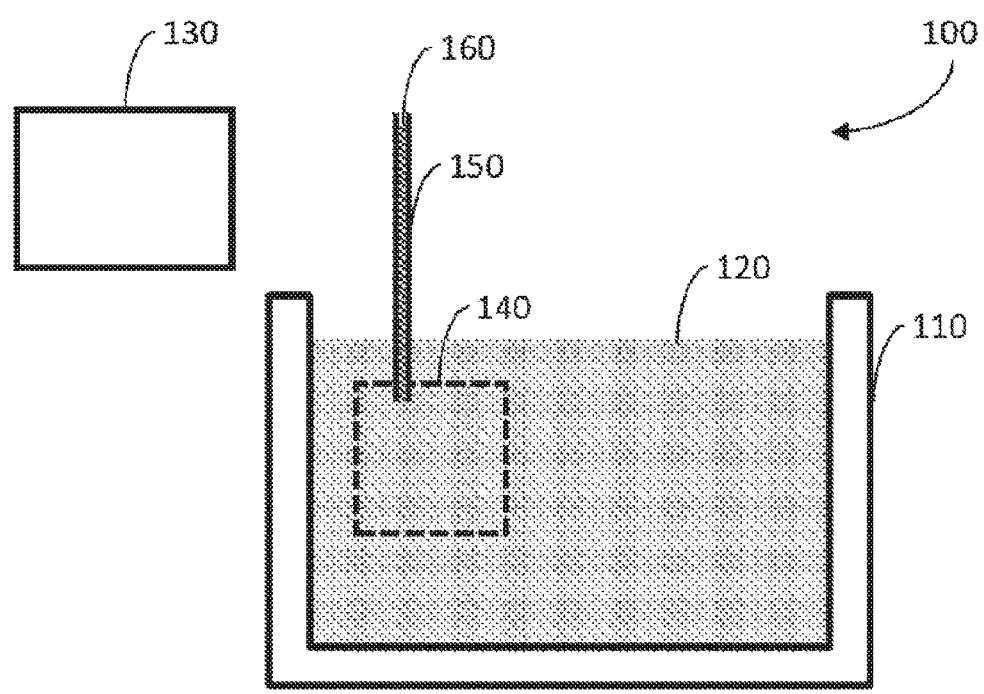
FIG. 1 is a schematic representation of one embodiment of an apparatus for placing cells in a 3D cell growth medium.

Disclosed herein is a 3D cell growth medium that allows for easy placement and/or retrieval of groups of cells and structures, which can be used to develop vascularized tissue. Although multiple cellular constructs have been tested for use in bone repair, success has been hindered by the inability to engineer a functional vascular network. Indeed vascularization currently stands as the single greatest obstacle to the engineering of tissues of clinically relevant size. A 3D cell growth medium using the materials described herein can allow for a cell growth environment which mimics the complex in vivo growth environment in which a vascular network may grow in a bone replacement.

The 3D growth medium may be used to support, in an appropriate relationship, components that may grow into a vascularized bone replacement. The 3D growth medium may also provide nutrients and other elements required for maintaining growing a viable vascular network.

The components may include a mechanical component, such as a biocompatible support scaffold. This scaffold can be natural or synthetic. For example, the scaffold can be derived from an autologous, allogenic or xenogenic graft. In other embodiments, the scaffold is engineered using biocompatible materials. For example, in some cases, the scaffold is producing by 3D printing, which can be done prior to deposit into the granular gel, or can be printed directly in the granular gel. For example, where the tissue is bone, the support scaffold can be a mineralized scaffold. In some cases, the support scaffold comprises decellularized bone, e.g. from a cadaveric donor. In other cases, the support scaffold comprises a porous scaffold formed from an osteogenic, osteoconductive, and/or osteoinductive material. For example, the scaffold can comprise hydroxyapatite.

Methods for 3D printing structures in granular gel are described in Bhattacharjee, T, et al. Science Advances, e1500655:1-6 (2015); Bhattacharjee, T, et al. ACS Biomat. Sci. & Eng., 2; 1787-1795 (2016); and O'Bryan, C S, et al. Science Advances, 3:e1602800 (2017), which are incorporated by reference for these teaches.

Additionally, the components may include a vascular structure capable of supporting blood flow. The vascular structure has at least one proximal and distal end in fluid communication. Therefore, in preferred embodiments, a distal end of the vascular structure is positioned in the granular gel in a location suitable to provide oxygen to the scaffold if blood is pumped into the proximal end of the vascular structure. In some embodiments, the vascular structure comprises an arterial or venous segment from a subject, such as a segment of an artery from a subject (autologous, allogenic, or xenogenic donor) to receive the bone replacement. In other embodiments, the vascular structure is a tissue engineered vessel. For example, the vessel can be produced using autologous, allogenic, or xenogenic endothelial cells, progenitor cells, or stem cells. It should be appreciated that the vascular structure may be any suitable structure capable of supporting blood flow if implanted into a recipient of the bone replacement.

Alternatively or additionally, the components may include a cellular component (marrow replacement) between the vascular structure and the mechanical component, and in some embodiment in pores or other interstices of the support component. This can be done before, after, or simultaneously with the deposit of the scaffold and/or the vascular structure. The choice of cellular component depends on the type of tissue being engineered. In some cases, the cellular component comprises one or more stem cells or progenitor cells capable of forming the desired tissue in the support scaffold. The cellular component can be positioned, for example, in the support scaffold, or between the support scaffold and the vascular structure. For example, where the tissue is bone, the cellular component can comprise bone marrow cells, or marrow-like cells. Therefore, in some embodiments, the cellular component comprises mesenchymal stem cells (MSCs), hematopoietic stem cells (HSCs), osteoblasts, osteocytes, angioblasts, or any combination thereof. The cellular component can further comprises growth factors that can promote angiogenesis, osteogenesis, and/or chondrogenesis, such as a vascular endothelial growth factor (VEGF), a fibroblast growth factor (FGF), an epidermal growth factor (EGF), an insulin-like growth factor (IGF), a bone morphogenetic protein 2 (BMP), or any combination thereof.

During a growth phase a blood-like fluid may be pumped through the vascular structure to provide oxygen and possibly other elements required for growth and viability of a capillary network through the bone replacement. Therefore, the method can then involve attaching a flow device to the proximal end of the vascular structure and flowing through the vascular structure a blood-like media sufficient to support tissue growth. Suitable flow devices are known, such as peristaltic pumps or syringe pumps. In some embodiments, the blood-like media comprises blood or a blood substitute, e.g. comprising oxygenated erythrocytes. In some embodiments, the blood-like media comprises an acellular endothelial growth medium.

In some embodiments, a 3D cell growth medium may comprise hydrogel particles dispersed in a liquid cell growth medium. Any suitable liquid cell growth medium may be used; a particular liquid cell growth medium may be chosen depending on the types of cells which are to be placed within the 3D cell growth medium. Suitable cell growth medium may be human cell growth medium, murine cell growth medium, bovine cell growth medium or any other suitable cell growth medium. Depending on the particular embodiment, hydrogel particles and liquid cell growth medium may be combined in any suitable combination. For example, in some embodiments, a 3D cell growth medium comprise approximately 0.5% to 1% hydrogel particles by weight.

In accordance with some embodiments, the hydrogel particles may be made from a bio-compatible polymer.

The hydrogel particles may swell with the liquid growth medium to form a granular gel material. Depending on the particular embodiment, the swollen hydrogel particles may have a characteristic size at the micron or submicron scales. For example, in some embodiments, the swollen hydrogel particles may have a size between about 0.1 µm and 100 µm. Furthermore, a 3D cell growth medium may have any suitable combination of mechanical properties, and in some embodiments, the mechanical properties may be tuned via the relative concentration of hydrogel particles and liquid cell growth medium. For example, a higher concentration of hydrogel particles may result in a 3D growth medium having a higher elastic modulus and/or a higher yield stress.

Tunability may be advantageous for controlling the environment around a group of cells placed in a 3D cell growth medium. For example, a 3D cell growth medium may have mechanical properties which are tuned to be similar to those found in vivo so that the cells 3D growth medium may emulate the natural environment of the cells. However it should be understood that the mechanical properties of a 3D cell growth medium may not be similar to those found in vivo, or may be tuned to any suitable values, as the disclosure is not so limited.

According to some embodiments, a 3D cell growth medium may be made from materials such that the granular gel material undergoes a temporary phase change due to an applied stress (e.g. a thixotropic or "yield stress" material). Such materials may be solids or in some other phase in which they retain their shape under applied stresses at levels below their yield stress. At applied stresses exceeding the yield stress, these materials may become fluids or in some other more malleable phase in which they may alter their shape. When the applied stress is removed, yield stress materials may become solid again. Stress may be applied to such materials in any suitable way. For example, energy may be added to such materials to create a phase change. The energy may be in any suitable form, including mechanical, electrical, radiant, or photonic, etc.

Providing a 3D cell growth medium made from a yield stress material, as described above, can enable facile placement and/or retrieval of a group cells at any desired location within the 3D growth medium. For example, placement of cells may be achieved by causing a solid to liquid phase change at a desired location in a region of yield stress material such that the yield stress material will flow and be displaced when cells are injected or otherwise placed at the desired location. After injection, the yield stress material may solidify around the placed cells, and therefore trap the cells at the desired location.

However, it should be appreciated that any suitable techniques may be used to deposit cells or other biological materials within the 3D growth medium. For example, using a syringe, pipette or other suitable tool, cells may be injected into one or more locations in the 3D growth medium. In some embodiments, the injected cells may be shaped as a pellet, such as by centrifugation. However, it should be appreciated that a 3D growth medium as described herein enables injection of cells suspended in a liquid, which may avoid a centrifugation step in conducting tests.

Moreover, it is not a requirement that the materials positioned in the 3D growth medium be liquid. In accordance with some embodiments, decellularized bone, a vascular structure, a marrow replacement and/or any other component that becomes the bone replacement may be inserted into the 3D growth medium and then may be partially or fully supported by the growth medium. Marrow replacement may be like a paste and may be injected, but other times, such as the decellularized bone, may simply be pressed into position.

Regardless of how cells or other items are placed in the medium, the yield stress of the yield stress material may be large enough to prevent yielding due to gravitational and/or diffusional forces exerted by the cells such that the position of the cells within the 3D growth medium may remain substantially constant over time. Since the cells are fixed in place, they may be retrieved from the same location at a later time for assaying or testing by causing a phase change in the yield stress material and removing the cells. However, it should be appreciated that, for more dense items, an external support structure may be used to partially support the item.

A yield stress material as described herein may have any suitable mechanical properties. For example, in some embodiments, a yield stress material may have an elastic modulus between of approximately 0.1 Pa to 1000 Pa (including 0.1 to 10 Pa; 1.0 to 10 Pa; 0.1 to 50 Pa; 1.0 to 50 Pa; 0.1 to 100 Pa; 1.0 to 100 Pa; 10 to 100 Pa; 100 to 500 Pa; or 500 to 1000 Pa) when in a solid phase or other phase in which the material retains its shape under applied stresses at levels below the yield stress. In some embodiments, the yield stress required to transform a yield stress material to a fluid-like phase may be between approximately 0.01 Pa and 1000 Pa (including 0.1 to 10 Pa; 1.0 to 10 Pa; 0.1 to 50 Pa; 1.0 to 50 Pa; 0.1 to 100 Pa; 1.0 to 100 Pa; 10 to 100 Pa; 100 to 500 Pa; or 500 to 1000 Pa). When transformed to a fluid-like phase; a yield stress material may have a viscosity between approximately 0.01 Pa s and 10,000 Pa s (including 0.1 to 10 Pa s; 1.0 to 10 Pa s; 1.0 to 100 Pa s; 10 to 100 Pa s; 10 to 1,000 Pa s; 100 to 1,000 Pa s; 100 to 10,000 Pa s; 1,000 to 10,000 Pa s; or 5,000 to 10,000 Pa s). However, it should be understood that other values for the elastic modulus, yield stress, and/or viscosity of a yield stress material are also possible, as the present disclosure is not so limited.

In some embodiments, the yield stress may be tuned to match the compressive stress experienced by cell groups in vivo; as described above. Without wishing to be bound by any particular theory, a yield stress material which yields at a well-defined stress value may allow indefinite and/or unrestricted growth or expansion of a group of cells. Specifically, as the group of cells grows, it may exert a hydrostatic pressure on the surrounding yield stress material; this hydrostatic stress may be sufficient to cause yielding of the yield stress material, thereby permitting expansion of the group of cells. In such embodiments, the yielding of the yield stress material during growth of a group of cells may result in the yield stress material maintaining a constant pressure on the group of cells during growth. Moreover; because a yield stress material will yield when an applied stress exceeds the yield stress, a 3D growth medium made from a yield stress material may not be able to apply a stress to a group of cells which exceeds the yield stress. Such an upper bound on the stress applied to a group of cells may help to ensure that cells are not unnaturally constrained, damaged or otherwise altered due to the application of large compressive stresses.

According to some embodiments, a 3D growth medium made from a yield stress material may yield to accommodate excretions such as fluids or other extracellular materials from a group of cells disposed within the 3D growth medium. Without wishing to be bound by any particular theory, excretion of fluids or other materials from a group of cells may result in an increase in the pressure in the extracellular space; if the pressure exceeds the yield stress of the 3D growth medium, the 3D growth medium may yield to accommodate the excretions; and a group of cells may excrete fluids or other materials without restriction. Such an ability of a 3D growth medium to accommodate cellular excretion may allow the 3D growth medium to more closely match an in vivo environment. Moreover, a 3D growth medium made from a yield stress material may allow for facile removal of cellular excretions for assaying, testing, or any other suitable purpose, as described in more detail below. In accordance with some embodiments, extraction of materials from the 3-D growth medium, which are then assayed, may provide data to control a system that impacts conditions within the growth medium. For example, the rate of exchange of growth medium in the vessel holding the 3-D growth medium may be modulated in response a measured concentration of enzymes, cellular secretions, nutrients, etc. determined by assaying medium extracted from the vessel.

According to some embodiments, a 3D cell growth medium made from a yield stress material may enable 3D printing of cells or other material, such as marrow replacement, to form a desired pattern in three dimensions. For example; a computer-controlled injector tip may trace out a spatial path within a 3D cell growth medium and inject cells at locations along the path to form a desired 3D pattern or shape. Movement of the injector tip through the 3D cell growth medium may impart sufficient mechanical energy to cause yielding in a region around the injector tip to allow the injector tip to easily move through the 3D cell growth medium, and also to accommodate injection of cells. After injection, the 3D cell growth medium may transform back into a solid-like phase to support the printed cells and maintain the printed geometry. However, it should be understood that 3D printing techniques are not required to use a 3D growth medium as described herein.

In some embodiments, a 3D cell growth medium may be used to support and/or preserve the structure of a cell-laden engineered tissue construct. For example, a tissue construct including a scaffold or other suitable structure on which a plurality of cells is disposed may be placed into a 3D cell culture medium. The 3D cell culture medium may provide support to preserve a complex structure of the tissue construct while also providing a 3D environment for cell growth which may mimic that found in vivo. Additionally, the cell growth medium may include extracellular matrix proteins, such as collagen or laminin, to improve cell function and more accurately recreate in vivo behavior.

The terms "yield stress" and "yield stress material" have been used and characterized in different ways in the art. For ease of description herein, the terms "yield stress" and "yield stress material" are used but, unless indicated otherwise, should be understood to be a Herschel-Bulkley yield stress determined using the Herschel-Bulkley equation $$\sigma = \sigma_y + k \bar{\gamma}^p$$

where $\sigma_y$ is yield stress, $\sigma$ is shear stress, k is viscosity index of the material, $\bar{\gamma}$ is shear rate, and p is a positive number, and a material having such a yield stress.

In addition, "yield stress" (i.e., Herschel-Bulkley yield stress) has been measured in different ways in the art. Unless indicated otherwise herein, a yield stress of a sample is determined by shearing the sample in a rheometer using plate-plate geometry and via the Herschel-Bulkley equation, via the following process. Prior to shearing, the rheometer tool surfaces may be roughened to prevent or mitigate slipping at the sample-tool interface. Using the rheometer, the sample is sheared at a variety of shear rates, extending from high shear rates (e.g., 1000 $s^{-1}$) to low shear rates (0.001 $s^{-1}$). For each shear rate, the sample is sheared for 30 seconds, after which shear stress data is collected and averaged. A series of shear stress measurements are collected sequentially for each shear rate. These shear rates are then used, via the Herschel-Bulkley equation, to determine (1) whether the material has a yield stress (i.e., a Herschel-Bulkley yield stress), and (2) the yield stress for the material. Those skilled in the art will appreciate that, for a material having a yield stress, a plot of shear stress versus shear rate will exhibit a plateau region at low shear rates, with the data points asymptotically approaching the material's yield stress at low shear rates. The yield stress is the shear stress at these low, near-zero shear rates, or an estimate of shear stress at zero strain rate determined using a low or near-zero shear rate, such as a shear rate of $10^{-3}$ $s^{-1}$. As used herein (unless indicated otherwise), a "yield stress material" will be a material that has a yield stress determinable via this process. Those skilled in the art will appreciate that for a yield stress material (i.e., a Herschel-Bulkley yield stress material) at low shear (e.g., a near-zero shear rate), a shear stress is independent of shear rate and instead exhibits only a shear stress dependent only on an elastic component of the material.

FIG. 1 is a schematic representation of one embodiment of an apparatus 100 for placing groups of cells in a 3D cell growth medium 120. The apparatus 100 may include a container 110, a focused energy source 130, and an injector 150. The container 110 may hold the 3D cell growth medium 120. The focused energy source 130 may cause a phase change in a region 140 of the 3D cell growth medium 120 by applying focused energy to the region 140. The injector 150 may displace the 3D cell growth medium 120 with a material 160 which may include a plurality of cells.

According to some embodiments, the container 110 may be a tub, a bowl, a box, or any other suitable container for the 3D cell growth medium 120. As described above, the 3D cell growth medium 120 may include a thixotropic or yield stress material, or any material suitable for temporary phase changing. Additionally, the cell growth medium 120 may include extracellular matrix proteins, such as collagen or laminin, to improve cell function and more accurately recreate in vivo behavior. In some examples, the thixotropic or yield stress material may include a soft granular gel. The soft granular gel may be made from polymeric hydrogel particles swelled with a liquid cell culture medium. Depending on the particular embodiment, the hydrogel particles may be between 0.5 μm and 50 μm in diameter, between about 1 μm and 10 μm in diameter, or about 5 μm in diameter when swelled.

Figure 2B:
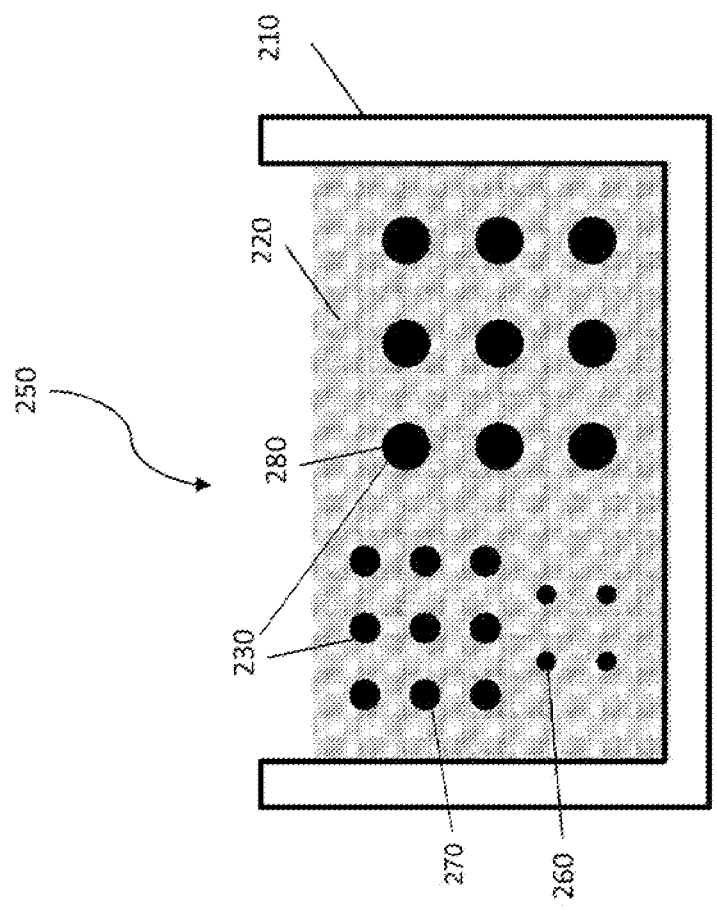
FIGS. 2A-2D are schematic representations of embodiments of a 3D cell growth medium including a plurality of cell spheroids.
Figure 2A:
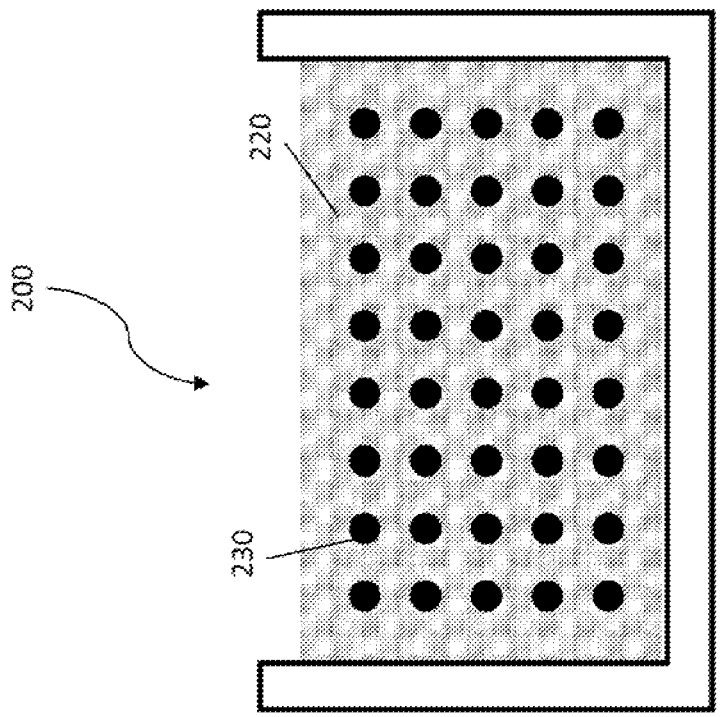

FIG. 2A depicts a cross sectional view of one embodiment of a 3D cell culture 200 including a 3D cell growth medium 220 disposed in a container 210. A plurality of spheroids 230 comprising one or more cells is arranged in the 3D cell growth medium 220. In the depicted embodiment, the spheroids 230 are approximately the same size and are spaced evenly spaced apart. In some embodiments, the spheroids may not all have the same size and/or spacing. For example, the FIG. 2B depicts another embodiment of a 3D cell culture 250 including small spheroids 260, intermediately sized spheroids 270, and large spheroids 280. In view of the above, it should be understood that cells spheroids of cells may have any suitable combination of sizes and/or spacing. Although spheroids are depicted, it should be understood that groups of cells may not be spheroid, and may be embryoid, organoid, torpid, or have any other suitable shape, as the disclosure is not so limited. In accordance with some embodiments, components of a bone replacement may be deposited in a shape desired for a portion of the bone replacement.

Figure 2C:
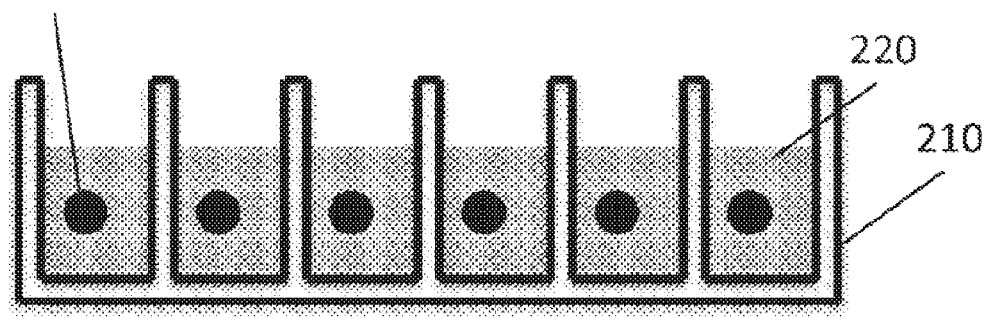
Figure 2D:
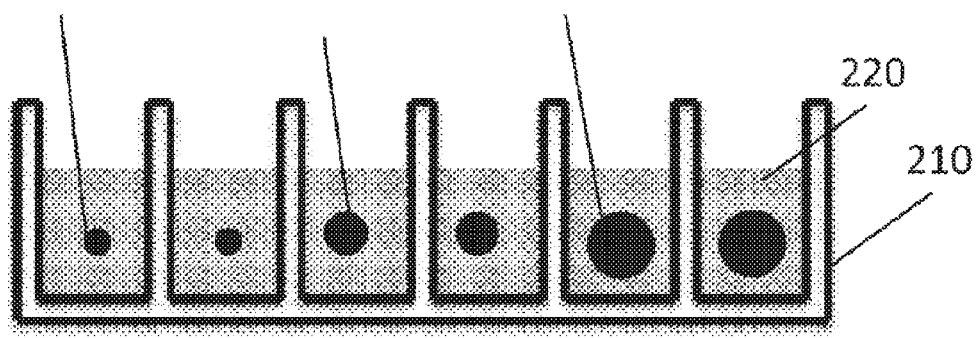

FIGS. 2A and 2B Figures illustrate the generation of multiple cell clusters, here shown as spheres, in the same vessel. FIGS. 2C and 2D illustrate the generation of multiple identical spheres or spheres of various sizes in numerous individual vessels. Vessels as illustrated may be formed in a tray 210 or other suitable carrier to facilitate high throughput testing. However, it should be appreciated, that any suitable vessel or vessels may be used.

It should be appreciated that one or more compounds may be deposited in conjunction with and/or adjacent to cells or other items in the 3-D growth medium. For example, soluble, non-cellular components could be deposited in conjunction with the cells. These might include structural proteins (e.g. collagens, laminins), signaling molecules (growth factors, cytokines, chemokines, peptides), chemical compounds (pharmacologic agents), nucleic acids (e.g. DNA, RNAs), and others (nano-particles, viruses, vectors for gene transfer). It should be understood that the embodiments of 3D cell growth media described herein are not limited to any particular types of cells. For example, various embodiments of 3D cell growth media may be used with animal, bacterial, plant, insect, or any other suitable types of cells. As an example, components of a bone replacement may be deposited in the 3-D growth medium during a time while cells grow to form a vascular network, such as a capillary network.

Figure 3:
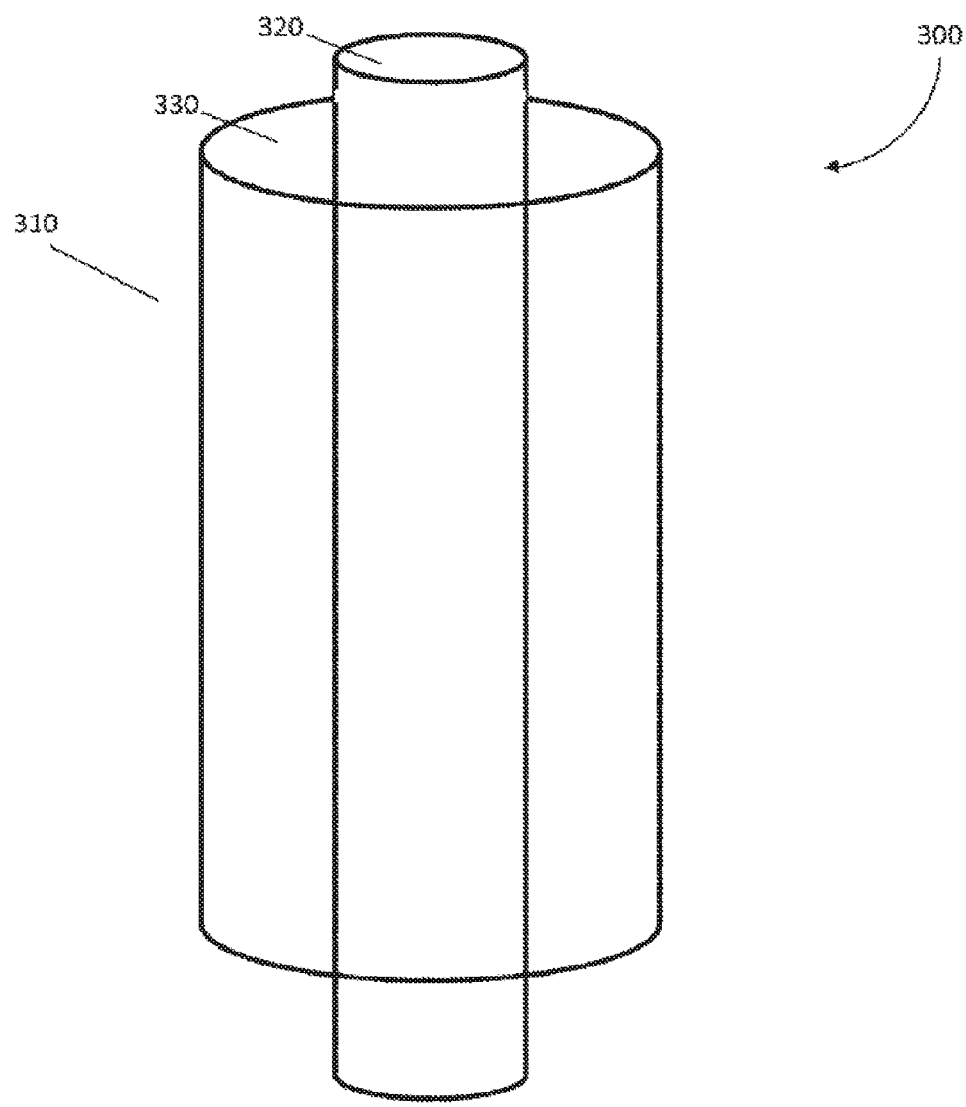
FIG. 3 is a schematic representation of a mineralized scaffold and autologous vascular tissue arrangement.

FIG. 3 illustrates a schematic representation of a scaffold and vascular tissue arrangement 300. In some embodiments, the scaffold may be a mineralized scaffold 310, which may be decellularized bone obtained from RTI in some embodiments. Such a structural component may be useful, for example, in applications requiring repair of large segmental defects. In other embodiments the mineralized scaffold 310 may be obtained from 3D biofabrication of collagen scaffolds and polymer induced liquid precursor mediated mineralization, for example in applications requiring generating irregular constructs of defined shape for repair of craniofacial skeletal defects.

Vascular tissue may be placed near the scaffold. In some embodiments, the vascular tissue may be autologous. The autologous vascular tissue 320 may be surgically harvested from the recipient subject in some embodiments. In other embodiments the autologous vascular tissue 320 may be obtained by 3D printing of ECM components and autologous MSCs and endothelial progenitor cells (EPCs) combined with vasculogenic growth factor stimulation. In still other embodiments, the autologous vascular tissue 320 may be obtained by recellularizing a commercial decellularized blood vessel with a culture media obtained from the patient recipient. The culture media may be deposited using 3-D printing techniques as described above, or in any other suitable way. The autologous vascular tissue 320 may be spatially positioned within the mineralized scaffold 310.

In some embodiments, a lumen 330 may exist in the mineralized scaffold 310 and the autologous vascular tissue 320 may pass through the lumen. In other embodiments, the mineralized scaffold 310 may contain no lumen 330, but the autologous vascular tissue 320 may be held in place by the 3-D growth medium. The entire arraignment 300 may be placed within a container containing a growth medium, as discussed above.

Regardless of the manner in which the scaffold and vascular tissue are held in place, space between them might be wholly or partially filled with material that may support the growth of a vascular network. For example, a marrow-like material, such as bone marrow paste, may fill space in lumen 330 between the vascular tissue and the scaffolding. In embodiments in which the scaffold does not have a lumen, the marrow-like material may nonetheless occupy a portion of the space between the vascular tissue and the scaffold to support capillary ingrowth into the scaffold.

Figure 4:
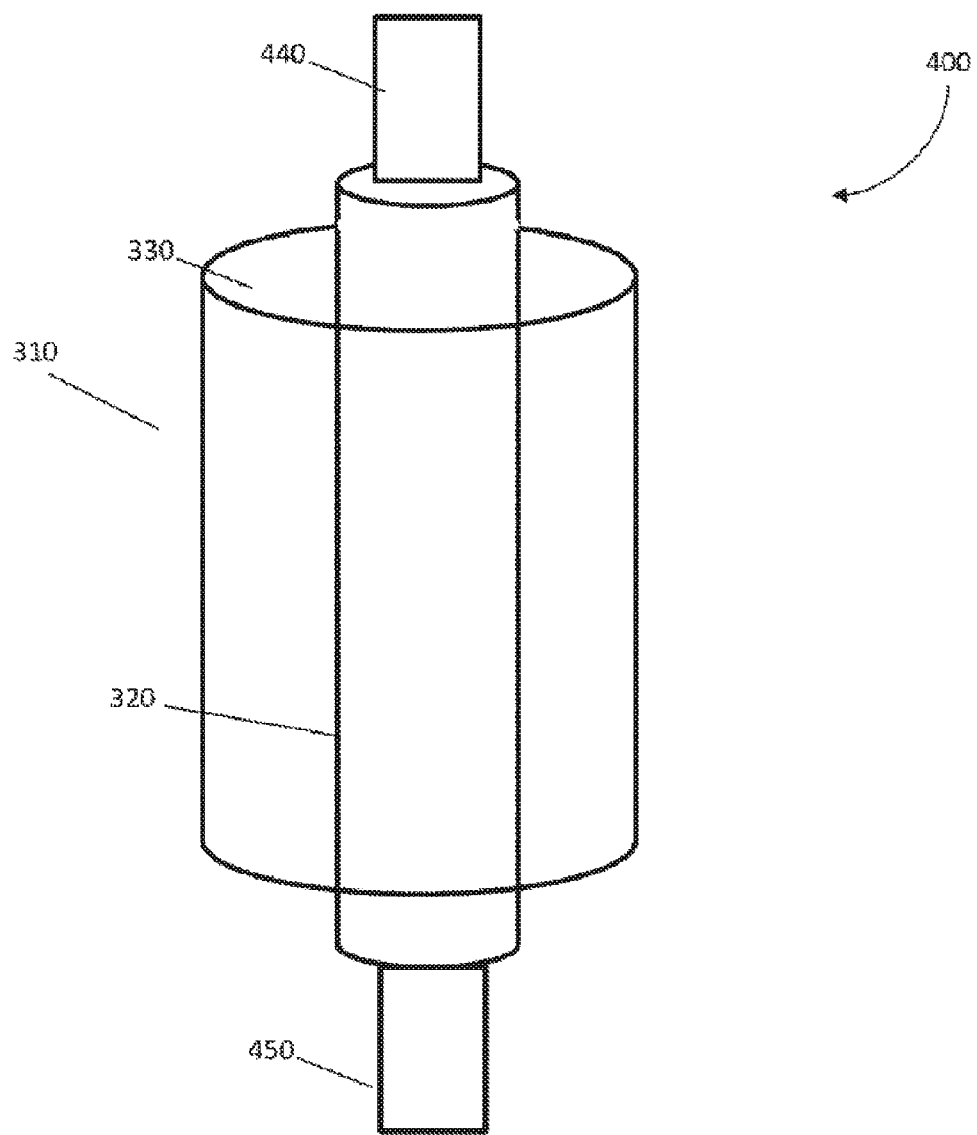
FIG. 4 is a schematic representation of a mineralized scaffold and autologous vascular tissue arrangement with pumps connected to the autologous vascular tissue.

FIG. 4 is another schematic of a mineralized scaffold and autologous vascular tissue arrangement 400. An upper flow device 440 may be connected to one end of the autologous vascular tissue 320. The upper flow device 440 may be any suitable device for moving a blood-like media, described below, through the autologous vascular tissue 320. A lower flow device 450 may be connected to another end of the autologous vascular tissue 320. The lower flow device 450 may be any device suitable to filter, oxygenate or otherwise re-condition or reconstitute the bloodlike medium and return it to the upper flow device 440. In some embodiments, only one flow device may be required. In other embodiments, two or more flow devices may be required, depending on the configuration of the autologous vascular tissue 320. The entire arraignment 400 may be placed within a container containing a growth medium, as discussed above. The blood-like media may be actual blood, such as from the recipient subject, or any appropriate substitute to be circulated continuously through the autologous vascular tissue 320 and a subsequent neo-tissue.

Figure 5:
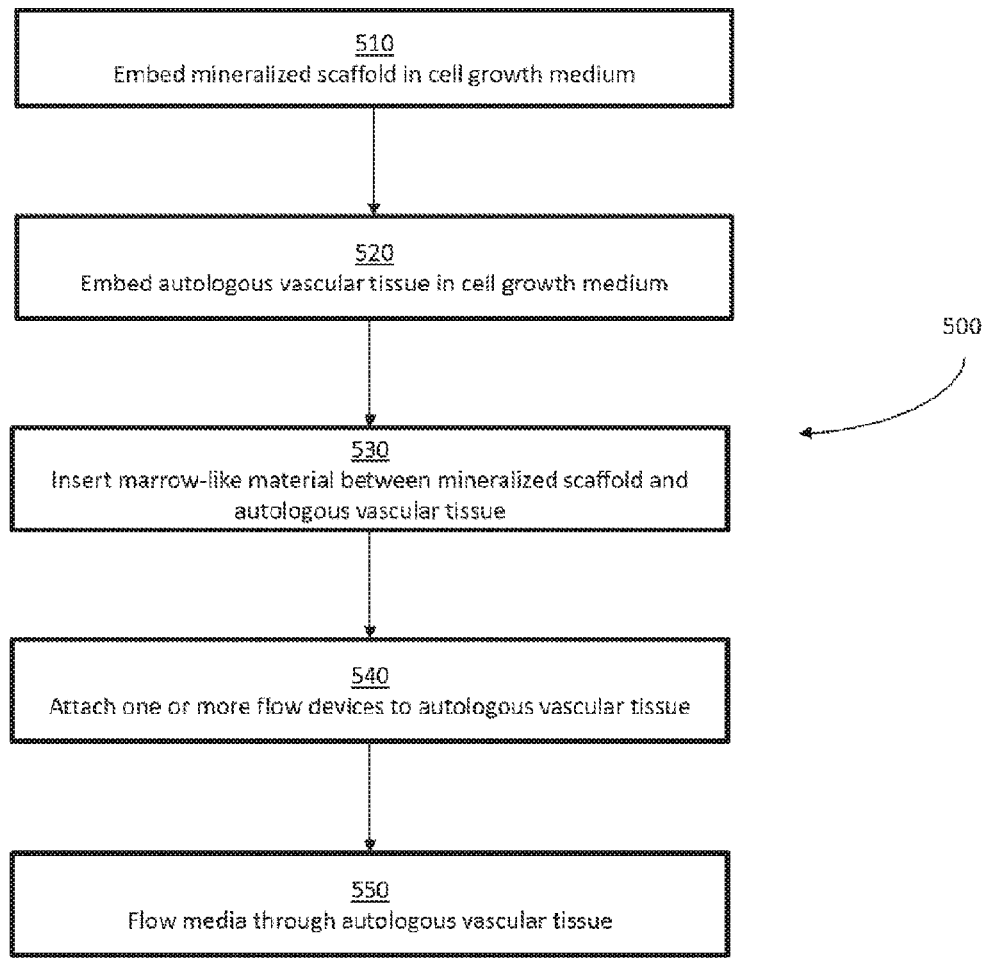
FIG. 5 is a flowchart of a method for growing a vascular network between an autologous vascular tissue and a mineralized scaffold.

FIG. 5 is a flowchart of a method 500 for growing a vascular network between an autologous vascular tissue and a mineralized scaffold. In Act 510, a mineralized scaffold, such as the one described in FIG. 3, may be embedded in a cell growth medium, such as the one described in FIG. 1. In Act 520, an autologous vascular tissue, such as the one described in FIG. 3, may be embedded in the cell growth medium. In Act 530, a marrow-like material may be inserted in a lumen between the mineralized scaffold and the autologous vascular tissue. The marrow-like material may comprise patient autologous MSCs and/or ECSs suspended in dilute demineralized bone matrix supplemented with VEGF, bFGF and/or EGF. The insertion of the marrow-like material may follow the method described in FIG. 6. The marrow-like material may serve as a marrow anlage for subsequent tissue maturation. In Act 540, one or more flow devices may be attached to the autologous vascular tissue. In Act 550, blood-like media may flow through the autologous vascular tissue via the one or more flow devices. This process may facilitate the formation of a vascular network from the autologous vascular tissue, which may vascularize the mineralized scaffold. The mineralized scaffold, once a mature vascular network is created, may be implanted in a patient recipient. The ordering of the acts should not be considered a limitation, in other embodiments the acts may occur in a different order. For example, Act 520 may occur before Act 510 in some embodiments.

Figure 6:
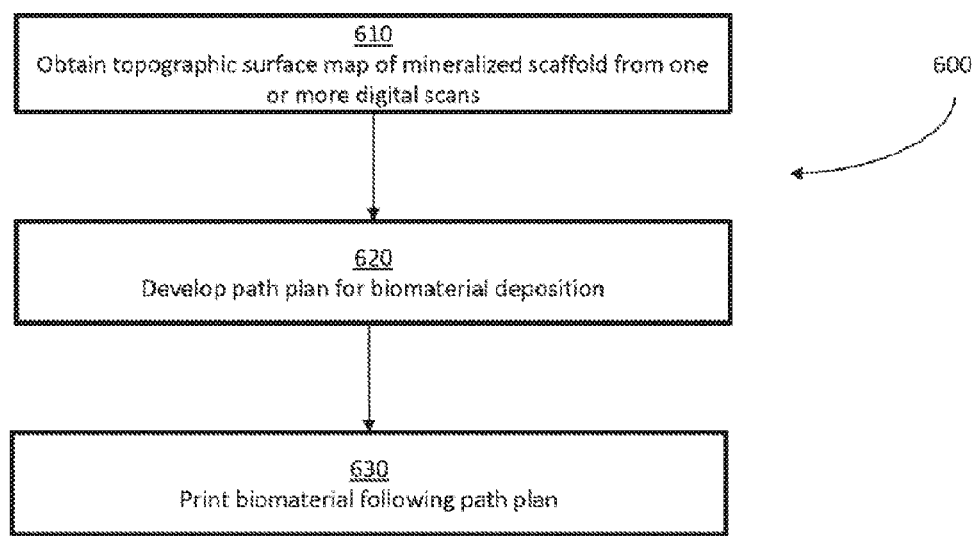
FIG. 6 is a flowchart of a method for 3D printing biomaterial following a path plan.

FIG. 6 is a flowchart of a method 600 for 3D printing biomaterial following a path plan. In Act 610 a topographic surface map of a mineralized scaffold may be obtained from one or more digital scans. The scans may be from MRI scans, micro-CT scans, or another suitable source. These scans may provide 3-D information about an injury or other location in a patients body where a bone replacement is to be surgically implanted. This information may be used to compute the dimensions of the bone replacement. In embodiments in which the scaffold is manufactured, the information may be used to derive parameters of the scaffold. In other embodiments, when the scaffold is harvested from a donor organism and thus has a predefined shape, the information may be used to determine how to apply other components of the bone replacement within or around the scaffold. Accordingly, the information from a scan of the patient may be used in any suitable way to guide the manufacture of the bone replacement. For example, it may define a topographic surface of material to be deposited in growth medium to form the bone replacement.

In Act 620, the topographic surface may be used to develop a path plan for biomaterial deposition on or within the mineralized scaffold. The path plan may follow a linear path, radial path, random droplet method or any other suitable path. In Act 630, biomaterial, such as the biomaterials described above, may be printed on or within the mineralized scaffold following the path plan. The printing may be done by an apparatus for placing cells in a 3D cell growth medium as described above.

A number of embodiments have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for engineering vascularized bone tissue, comprising
providing a three-dimensional (3D) cell growth medium comprising a plurality of hydrogel particles and a liquid cell culture medium, wherein the hydrogel particles are swelled with the liquid cell culture medium to form a granular gel, wherein the three-dimensional cell growth medium has a yield stress such that the cell growth medium undergoes a phase change from a first solid phase to a second liquid phase upon application of a shear stress greater than the yield stress;
depositing into the granular gel a biocompatible support scaffold comprising decellularized bone;
depositing into a cavity of the support scaffold a vascular structure capable of supporting blood flow, wherein the vascular structure has a proximal and distal end;
depositing into the granular gel a cellular component, wherein the cellular component comprises one or more stem cells or progenitor cells capable of forming tissue in the support scaffold, wherein the cellular component is positioned in the support scaffold, or between the support scaffold and the vascular structure;
depositing into the granular gel one or more angiogenic growth factors at locations to promote angiogenesis and vasculogenesis in the support scaffold;
attaching a flow device to the proximal end of the vascular structure; and
flowing through the vascular structure a blood-like media sufficient to support tissue growth.

2. The method of claim 1, wherein the vascular structure comprises an arterial or venous segment from a subject.

3. The method of claim 1, wherein the cellular component comprises mesenchymal stem cells (MSCs), hematopoietic stem cells (HSCs), osteoblasts, osteocytes, angioblasts, or any combination thereof.

4. The method of claim 1, wherein angiogenic growth factors comprise vascular endothelial growth factor (VEGF), basic fibroblast growth factor (bFGF), epidermal growth factor (EGF), or any combination thereof.

5. The method of claim 1, wherein the blood-like media comprises blood or a blood substitute comprising oxygenated erythrocytes.

6. The method of claim 1, wherein the yield stress is on the order of 10 Pa+/−25%.

7. The method of claim 1, wherein the concentration of hydrogel particles is between 0.05% to about 1.0% by weight.

8. The method of claim 1, wherein the hydrogel particles have a size in the range of about 0.1 µm to about 100 µm when swollen with the liquid cell culture medium.

9. The method of claim 8, wherein the hydrogel particles have a size in the range of about 1 µm to about 10 µm when swollen with the liquid cell culture medium.

10. The method of claim 1, further comprising molecules diffused into the granular gel particles and throughout the granular gel.

11. The method of claim 10, wherein the molecules comprise small molecules or proteins.

12. The method of claim 11, wherein the molecules are small molecules, and wherein the small molecules comprise nutrients or dissolved gasses.

* * * * *